United States Patent [19]

Shishido

[11] 4,440,157
[45] Apr. 3, 1984

[54] HARD ENDOSCOPE

[75] Inventor: Yoshio Shishido, Sagamihara, Japan

[73] Assignee: Olympus Optical Co., Ltd., Tokyo, Japan

[21] Appl. No.: 344,952

[22] Filed: Feb. 2, 1982

[30] Foreign Application Priority Data

Feb. 3, 1981 [JP] Japan ................... 56-14545

[51] Int. Cl.³ ............................................. A61B 1/04
[52] U.S. Cl. ........................................ 128/6; 354/62
[58] Field of Search ............................. 128/3-11, 128/303.1; 354/62, 79, 222; 352/131

[56] References Cited

U.S. PATENT DOCUMENTS

| | | | |
|---|---|---|---|
| 3,638,643 | 2/1972 | Hotchkiss | 354/62 X |
| 3,925,793 | 12/1975 | Matsumura et al. | 354/62 |
| 4,068,932 | 1/1978 | Ohta et al. | 354/62 X |
| 4,102,563 | 7/1978 | Matsumura et al. | 354/62 X |
| 4,196,990 | 4/1980 | Forsyth | 354/62 |
| 4,251,139 | 2/1981 | Matsumura | 354/62 X |
| 4,264,167 | 4/1981 | Plummer | 354/62 |

Primary Examiner—Lee S. Cohen
Assistant Examiner—Angela D. Sykes
Attorney, Agent, or Firm—Armstrong, Nikaido, Marmelstein & Kubovcik

[57] ABSTRACT

A hard endoscope which can be removably fitted with a photographing device in the eyepiece part and by which, for example, a body cavity in which it is inserted can be observed and photographed is disclosed. In the case of taking a photograph with a hard endoscope fitted with a photographing device in the eyepiece part, if the optical axis of the hard endoscope and the optical axis of the photographing device do not coincide with each other and are eccentric from each other, the image obtained in the photographing device will differ from that seen by the endoscope. Therefore, the hard endoscope of this invention is provided in the eyepiece part with an eccentricity controlling means which can center the optical axis of the hard endoscope to coincide with the optical axis of the photographing device.

5 Claims, 10 Drawing Figures

HARD ENDOSCOPE

BACKGROUND OF THE INVENTION

This invention relates to endoscopes which can take photographs as combined with any photographing devices and more particularly to a hard endoscope having a relay lens system in the observing optical system.

Generally, a photographing device is fitted through a photographing adapter to the eyepiece part of an endoscope and, for example, a body cavity in which the inserted part of the endoscope is inserted is photograhed and diagnosed. However, if the optical axis of the endoscope and the optical axis of the photographing adapter or photograhing device do not coincide with each other and are eccentric from each other, the image obtained in the photographing device will differ from that seen by the endoscope. Therefore, the eccentricity of the optical axis of the endoscope side has been controlled by an eccentricity controlling means provided on the photographing device side. However, since the above mentioned eccentricity is different in each endoscope, it will be necessary to control the eccentricity whenever the above mentioned photographing device is fitted to the eyepiece part of each endoscope.

In order to solve this disadvantage, an image guide fixing device of an endoscope eyepiece part is disclosed in Japanese Utility Model Laid Open Publication No. 126801/1980. This device is so formed that, in a soft endoscope in which the observing optical system for transmitting images is formed of a fiber bundle, the above mentioned eccentricity is forcibly controlled, for example, with three-point lock screws by utilizing the flexibility of the above mentioned fiber bundle. However, in the hard endoscope in which images are transmitted by the relay lens system, it is impossible to forcibly easily adjust the image transmitting optical system as in the above mentioned device disclosed in Japanese Utility Model Laid Open Publication No. 126801/1980.

Further, as in the adapter device disclosed in U.S. Pat. No. 4,196,990, it is possible to control the above mentioned eccentricity by moving a vision field mask to a false focusing position. However, if the vision field mask is thus moved, the entire image will be deviated from the optical axis of the endoscope eyepiece and the resolving power and picture quality will be reduced. This is not desirable.

BRIEF SUMMARY OF THE INVENTION

An object of the present invention is to provide a hard endoscope wherein the eccentricity between the optical axis of the optical system of the hard endoscope and the optical axis of the photographing device can be controlled so as to be minimized or eliminated. Further, the nonuniformity produced in the image of the photographing device by the above mentioned eccentricity can be prevented and the image is easy to see without a sense of difference.

Another object of the present invention is to provide a hard endoscope whereby the center image of the endoscope image, that is, the target position to be photographed by the photographer can be caught and photographed in the center axis of the optical system where the aberrations are small.

Another further object of the present invention is to provide a hard endoscope wherein the eccentricity of the optical axis of the above mentioned hard endoscope and the optical axis of the photographing device can be minimized or eliminated without applying any unreasonable force to the observing optical system of the hard endoscope.

Another object of the present invention is to provide a hard endoscope wherein no centering mechanism is required on the photographing device.

Other further objects, features and advantages of the present invention will become apparent enough from the following explanation.

DETAILED DESCRIPTION OF THE INVENTION

Figure 1:
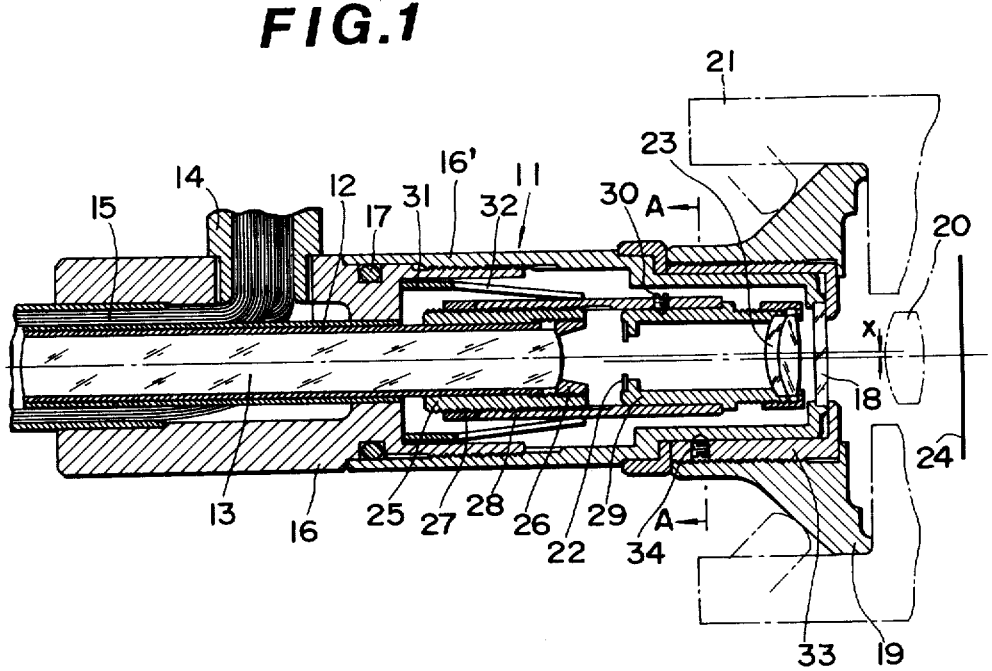
FIG. 1 is a vertically sectioned view showing an eyepiece part or operating part of a hard endoscope according to a first embodiment of the present invention.

A hard endoscope of a first embodiment of the present invention shall be explained with reference to FIGS. 1 to 4. In these drawings, the reference numeral 11 denotes an operating part of an endoscope in which a relay lens 13 fitted within a pipe 12 is arranged and is extended out to the rear of an objective at the front end of an inserted part of the endoscope and further a light guide 15 connected to a light source device through a joint 14 and flexible cable is fitted on the outer periphery of this pipe 12 and is extended out to the front end of the above mentioned inserted part of the endoscope. An outer tube 16' is screwed through an O-ring 17 in the rear of the body 16 of the above mentioned operating part 11 and an eyepiece frame 19 having an eyepiece window 18 is screwed to the rear end of this outer tube 16'. The mating surfaces of the outer tube 16' and body 16 are sealed by an O-ring 17 placed in a recess in the body 16. By the way, an $N_2$ gas for preventing the frosting of the optical system is enclosed within this hard endoscope. A photographing device is made to be removably fitted to the eyepiece frame 19 of the operating part body 16 through a photographing adapter 21 having a photographing lens 20 so that, for example, an internal organ within the body cavity in which the inserted part of the endoscope is inserted will be illuminated by the above mentioned light guide 15, an image will be transmitted through an objective not illustrated at the front end of the inserted part of the endoscope and the relay lens 13, will be focused though the vision field mask 22, for example, on the film face 24 of the photographing device by an eyepiece 23 and the photographing lens 20.

The above mentioned relay lens 13 is fixed at the rear end by screwing a lens fixing nut 26 on the rear inner periphery of a fixing frame 25 affixed by soldering to the rear outer periphery of the pipe 12. Further, a focusing frame 28 of the eyepiece 23 fixed by a lock nut 27 is screwed to this fixing frame 25. A fitting frame 29 having the above mentioned vision field mask 22 at the front end and the objective 23 at the rear end is fixed to this focusing frame 28 by a screw 30. The reference numeral 31 denotes an optical system holding part having a male screw on the outer periphery on the front end side, screwed on a female screw formed on the inner periphery on the rear side of the operating part body 16 and having tapered holding pieces 32 forming splits in the rear. The above mentioned focusing frame 28 is held on the inner periphery of the holding pieces 32 and is affixed with a binder or by soldering so that the above mentioned observing optical system can be held and fixed without applying a substantial force.

Figure 3:
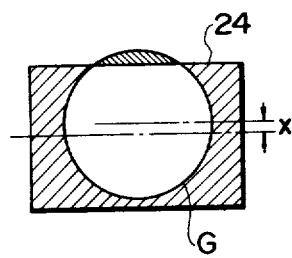
FIG. 3 is a plan view showing the state of a photographed image in the case where the optical axis of the observing optical system of a hard endoscope and the optical axis of the photographing device side are eccentric from each other.

Now, in the thus formed hard endoscope, if the axial position of the above mentioned observing optical system is eccentric, the eccentricity will not be able to be controlled as in a soft endoscope using an image fiber bundle and further the eccentricty errors arising from making and assembling the focusing frame 28 fixed by the lock nut 27 of the focusing means, the eyepiece fitting frame 29 and the photographing adapted 21 fitting eyepiece frame 19 will be added. In some cases, the eccentricity x, that is, the deviation between the center of the eyepiece frame 19 and the center of the eyepiece 23 will reach, for example, 1 mm. If the photographing device is fitted to a hard endoscope having this eccentricity x through the photographing adapter 21, the deviation x will be produced between the optical axis of the observing optical system of the hard endoscope and the optical axis of the photographing device and, as shown in FIG. 3, the eccentricity x will be produced between the center axis, for example, of the film face of the photographing device and the center axis of the image G and a portion of the observed image will not appear in the photographed image.

Figure 2:
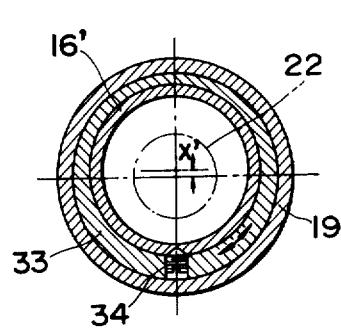
FIG. 2 is a sectioned view on line A—A in FIG. 1.

Therefore, according to the present invention, in the above mentioned formation, the centering frame 33 which is eccentric is fitted between the outer tube 16' and the eyepiece frame 19 so that, as shown in FIG. 2, the centering frame 33 is rotated in the direction in which the eccentricity x coincides with the center of the outer peripheral circle of the centering frame 33 and, after the eccentricity x coincides with the center of the outer peripheral circle of the above mentioned centering frame 33, the outer tube 16' and centering frame 33 are locked with a lock screw 34. By this formation and operation, the above mentioned eccentricity x can be minimized or eliminated.

By the way, this centering method is carried out by using an eccentricity controlling jig not illustrated having a screen concentric with the outer peripheral circle of the centering frame 33 and having crossed lines in the center position of the focusing lens.

Figure 4:
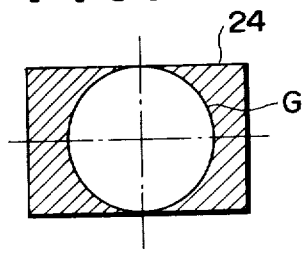
FIG. 4 is a plan view showing the state of a photographed image after the eccentricity in FIG. 3 is controlled by the eccentricity controlling means of the present invention.

After the eccentricity, that is, the deviation between the center of the eyepiece frame 19 and the center of the vision field mask 22 and eyepiece 23 is controlled, if the photographing device is fitted to the eyepiece frame 19 of the hard endoscope through the photographing adapter 21, the deviation between the optical axis of the observing optical system of the endoscope and the optical axis of the photographing device will be minimized or eliminated and, as shown in FIG. 4, the eccentricity of the center axis, for example, of the film face 24 of the photographing device and the center axis of the image G from each other will be minimized or eliminated.

Figure 5:
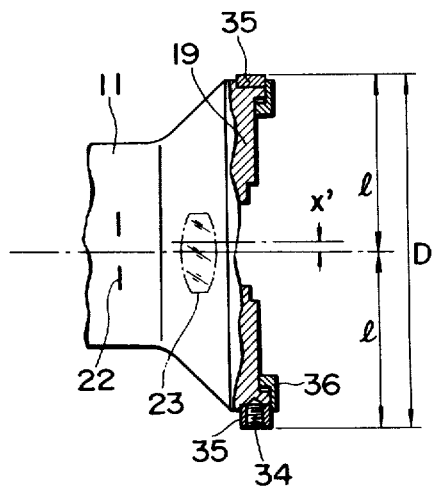
FIG. 5 is a partly sectioned elevation showing an eyepiece part of a second embodiment of the present invention.

FIG. 5 shows a second embodiment of the present invention. In this embodiment, an eccentric centering ring 35 is fitted to the outer periphery of the eyepiece frame 19 in advance and is rotated and adjusted to make the eccentricity x' coincide with the center of the eyepiece part fitting diameter D (radius 1) and, after the eccentricity x' coincides, the centering ring 35 and eyepiece frame 19 are locked with the lock screw 34 and further the fixing frame 36 is screwed to the eyepiece frame 19 so that the centering ring 35 may not come off.

By this formation, the eccentricity x' between the center of the vision field mask 22 and eyepiece 23 and the center of the eyepiece frame 19 will be absorbed in the proper rotating position of the centering ring 35.

Figure 6:
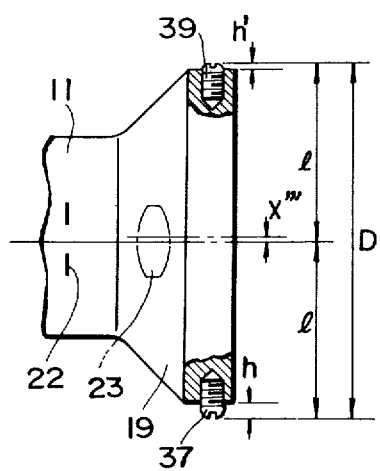
FIG. 6 is a partly sectioned elevation showing an eyepiece part of a third embodiment of the present invention.
Figure 7:
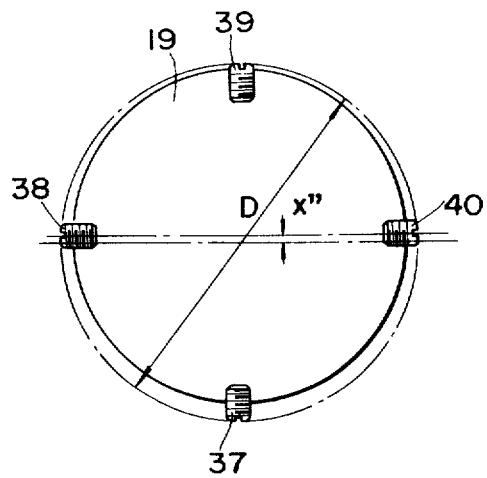
FIG. 7 is a plan view explaining FIG. 6.

FIGS. 6 and 7 show a third embodiment of the present invention. In this embodiment, eccentricity controlling screws 37, 38, 39 and 40 displaced 90° from each other are screwed to the outer periphery of the eyepiece frame 19, are individually adjusted in the heights h, h', so as to internally contact the eyepiece part fitting diameter D to absorb the eccentricity x" and are then bonded and fixed.

Figure 8:
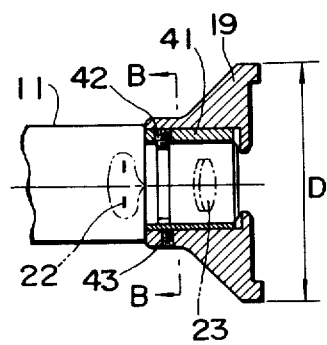
FIG. 8 is a sectioned view of an essential part showing an eyepiece part of a fourth embodiment of the present invention.
Figure 9:
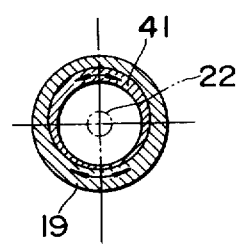
FIG. 9 is a sectioned view on line B—B in FIG. 8.
Figure 10:
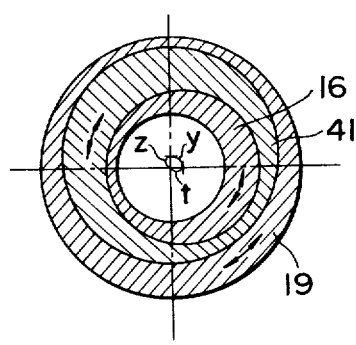
FIG. 10 is an explanatory cross-sectioned view of FIG. 8.

FIGS. 8 to 10 shown a fourth embodiment of the present invention. In this embodiment, not only the same eccentric centering frame 41 as in the first and second embodiments is provided but also the eyepiece frame 19 is made eccentric. The reference numerals 42 and 43 denote lock screws. In this formation, when the eccentricity between the vision field mask 22 and operating part body 16 is represented by T, the eccentricity between the operating part body 16 and centering frame 41 is represented by Y and the eccentricity between the centering frame 41 and eyepiece frame 19 is represented by Z, if $T+Y \geq Z$ is satisfied, it will be possible to make the eccentricity zero by adjusting the center of the fitting diameter D of the eyepiece part to which the photographing adapter is fitted and the image center of the vision field mask 22 by rotating the respective eccentric frames. By the way, in the first and second embodiments, as there is one centering means, the eccentricity can be minimized but will not be always made zero, will become zero only when $T=Y$ and will slightly remain.

By the way, in the present invention, 35 mm. cameras, 16 mm. cinematic cameras and television cameras are used for the photographing devices.

As it is apparent that different working modes can be formed in a wide range without departing from the spirit and scope of the present invention, the invention is not to be restricted by the specific working mode except being limited in the appended claims.

I claim:

1. In a hard endoscope having an outer tube and an observing optical system fixed therein through which an image may be observed, said optical system defining an observing optical axis, and an eyepiece frame having an inner surface and an outer periphery, said eyepiece frame mounted on said outer tube substantially concentric with said observing optical axis for removably supports a photographing device having a photographing optical axis for photographing through said observing optical system, wherein eccentricity may occur between said photographing optical axis and said observing optical axis, the improvement comprising eccentricity controlling means forming a part of said eyepiece frame for adjustably positioning said photographing optical axis with respect to said observing optical axis.

2. The improvement defined in claim 1, wherein said eccentricity controlling means comprises an eccentric centering frame rotatably positioned between the inner surface of said eyepiece frame and said outer tube.

3. The improvement defined in claim 1, wherein said eccentricity controlling means comprises an eccentric centering ring rotatably fitted to the outer periphery of said eyepiece frame.

4. The improvement defined in claim 1, wherein said eccentricity controlling means comprises a plurality of radially adjustable set screws positioned around the outer periphery of said eyepiece frame providing adjustable projections upon which said photographing device is supported.

5. The improvement defined in claim 1, wherein said eccentricity controlling means comprises an eccentric centering frame rotatably positioned between the inner surface of said eyepiece frame and said outer tube, said eyepiece frame being eccentrically mounted upon said eccentric centering frame for rotation thereon.

* * * * *